Figure 1:
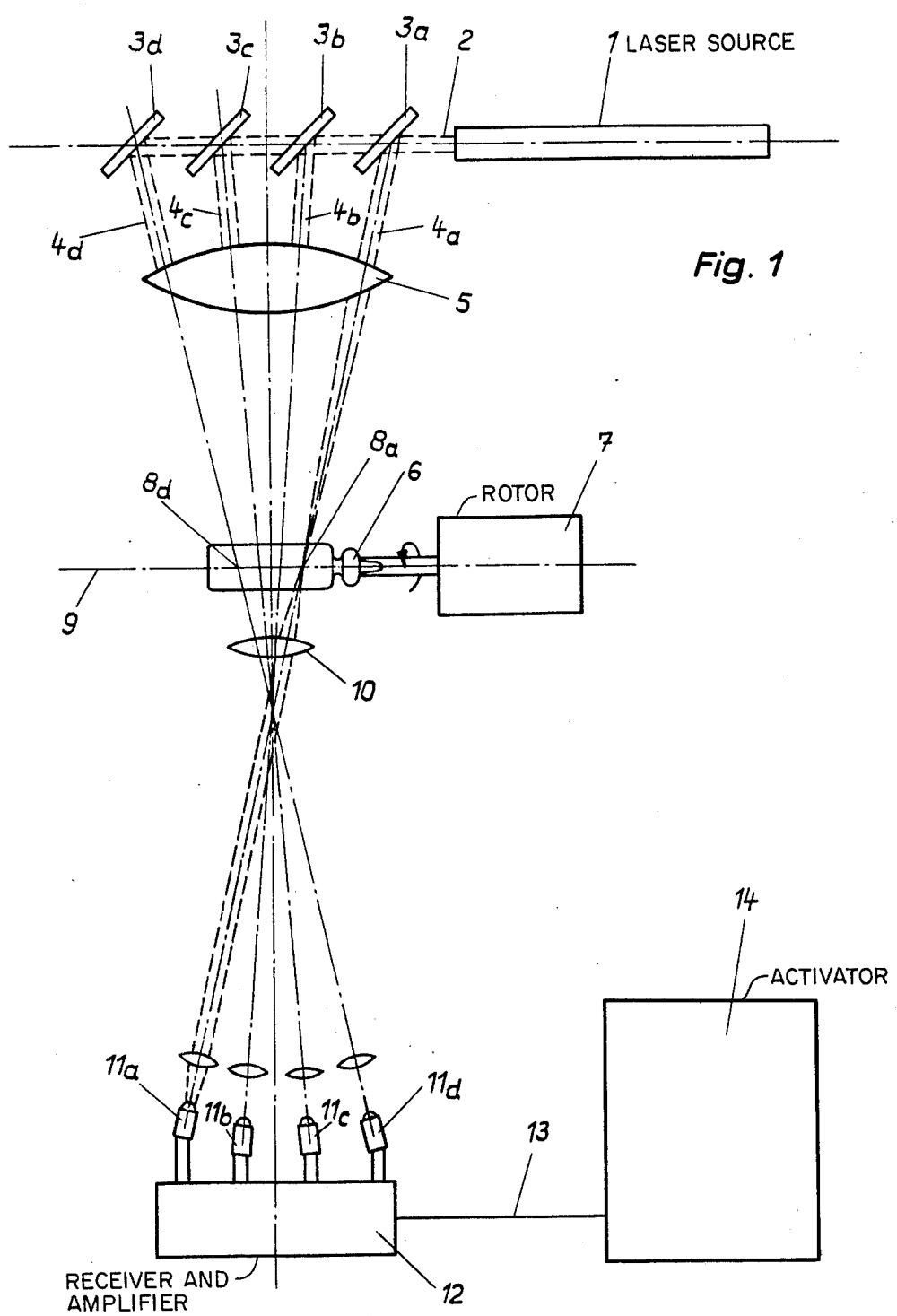

United States Patent [19]

Farcinade

[11] 4,028,553
[45] June 7, 1977

[54] APPARATUS FOR CONTROLLING PHARMACEUTICAL AMPOULES

[76] Inventor: Michel Farcinade, 19, rue des Delices, 1203 Geneva, Switzerland

[22] Filed: June 17, 1975

[21] Appl. No.: 587,759

[30] Foreign Application Priority Data

June 27, 1974 Switzerland .................. 8874/74
May 26, 1975 Switzerland .................. 6680/75

[52] U.S. Cl. .................. 250/576; 250/227; 250/573; 356/197; 356/196
[51] Int. Cl.² .................. G01N 21/26
[58] Field of Search .......... 250/208, 575, 576, 573, 250/571, 223 B, 227; 356/196, 197

[56] References Cited
UNITED STATES PATENTS

| | | | |
|---|---|---|---|
| 2,531,529 | 11/1950 | Price | 356/197 |
| 2,635,194 | 4/1953 | Kellogg et al. | 250/576 |
| 3,470,377 | 9/1969 | Le Febre et al. | 250/208 |
| 3,758,215 | 9/1973 | Paruolo et al. | 356/196 |
| 3,760,184 | 9/1973 | Brose | 250/571 |
| 3,766,489 | 10/1973 | Rosenberg et al. | 250/576 |
| 3,858,851 | 1/1975 | Ogle | 356/197 |
| 3,892,468 | 7/1975 | Duguay | 250/227 |
| 3,900,266 | 8/1975 | Takahashi et al. | 356/197 |

*Primary Examiner*—Eli Lieberman
*Assistant Examiner*—David K. Moore
*Attorney, Agent, or Firm*—Ladas, Parry, Von Gehr, Goldsmith & Deschamps

[57] ABSTRACT

An apparatus for examining vertically-held stationary pharmaceutical ampoules containing an injectable liquid, after having rotated the ampoules to spin the liquid and any foreign particles in the liquid, comprises a laser source emitting a beam which is directed vertically through an ampoule to be examined by one or more objectives. A series of photoelectric cells receive the beam, possibly via fiber bundles, and influence a circuit providing a signal for rejection of an ampoule containing a moving particle. The laser beam may be divided into several beams by partially reflecting mirrors, or a single beam passed through an ampoule several times by means of oblique mirrors.

1 Claim, 5 Drawing Figures

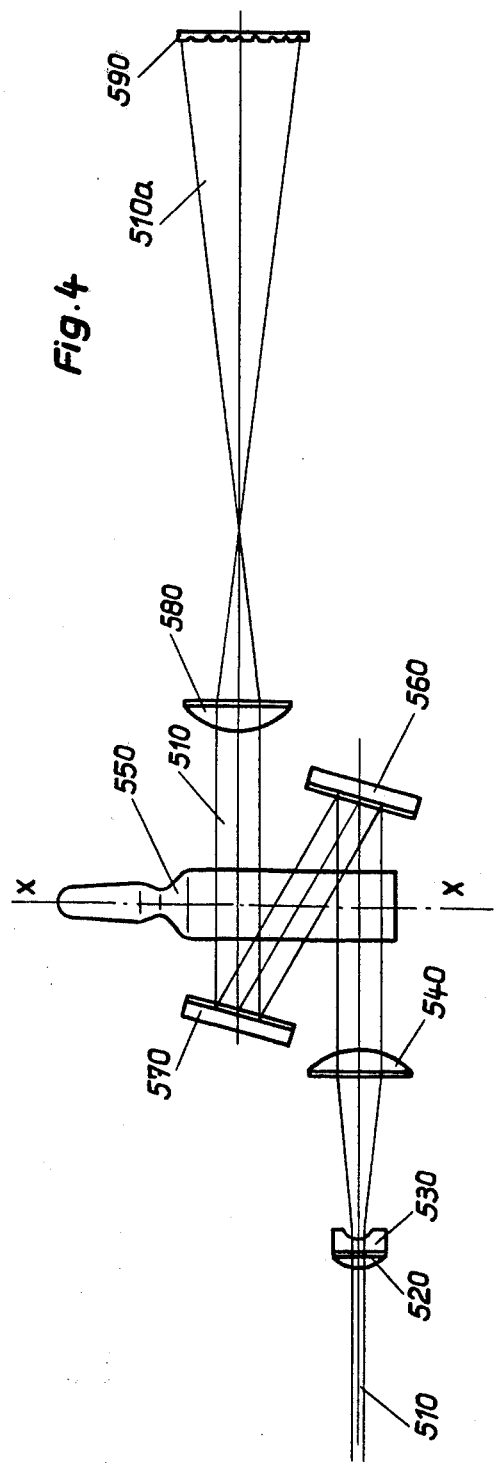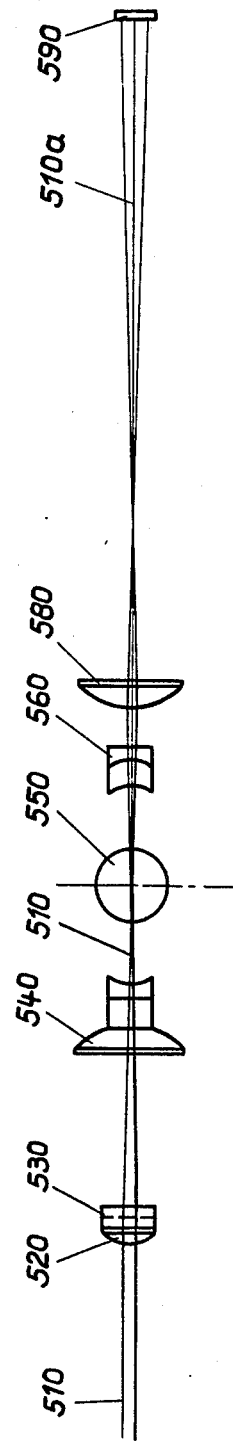

APPARATUS FOR CONTROLLING PHARMACEUTICAL AMPOULES

The invention concerns apparatus for examining pharmaceutical ampoules containing an injectable liquid, of the type comprising means for projecting light through a vertically-held ampoule to be examined, means for rotating this ampoule prior to an examination and for holding it without rotation during the examination, and means for observing the light having passed through the ampoule while at rest.

In known apparatus of this type, the light having passed through the ampoule while at rest is observed visually by a person against a background of bright light. However, these apparatus have the following disadvantages:

- the visual examination is tiring and requires, in addition to an excellent eyesight, a sustained attention;
- when fatigue occurs, the examination is uncertain while being costly;
- finally, the examination is subjective and an ampoule accepted by one examiner may b refused by another or even by the same examiner if the ampoule is returned to him incognito.

Now, it is clear that hermetically-closed pharmaceutical ampoules of glass containing a liquid substance for injection into the circulatory system must be submitted to a reliable examination to detect possible foreign bodies which could cause circulatory troubles.

An aim of the invention is to provide an apparatus enabling an improved and objective examination of such ampoules and avoiding the disadvantages of the known apparatus and methods.

According to the invention, an apparatus of the aforementioned type is therefore characterized in that the light-projecting means comprises a laser beam source and at least one lens means placed between the source and a held ampoule to produce a beam in a vertical plane passing through the ampoule to be examined, and that the light-observing device comprises a series of photoelectric cells each disposed to receive at least a part of the beam, and electrical means influenced by the cells for emitting a signal as a function of modifications of the beam in time produced by impurities moving in the liquid.

Figure 2:
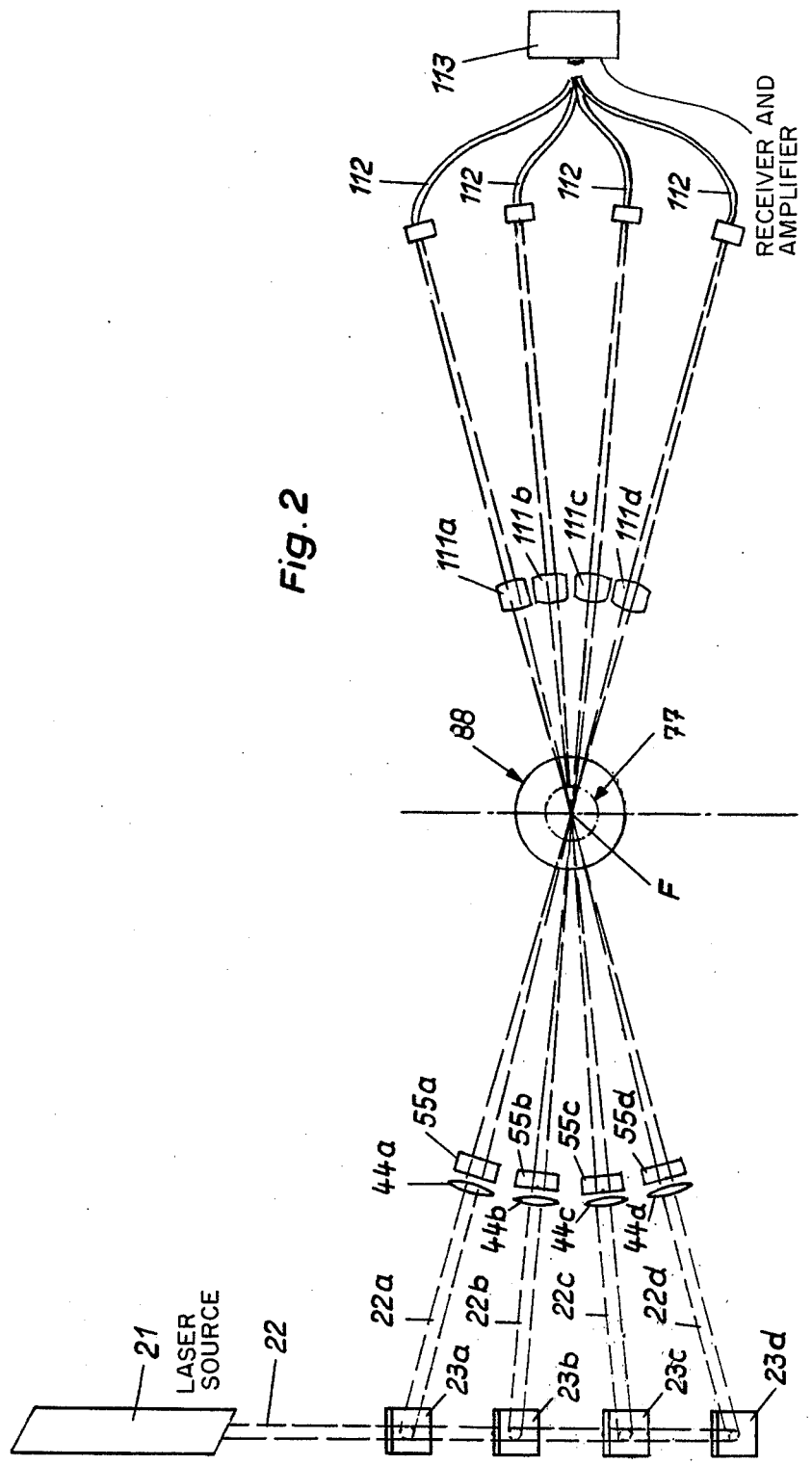
Figure 3:
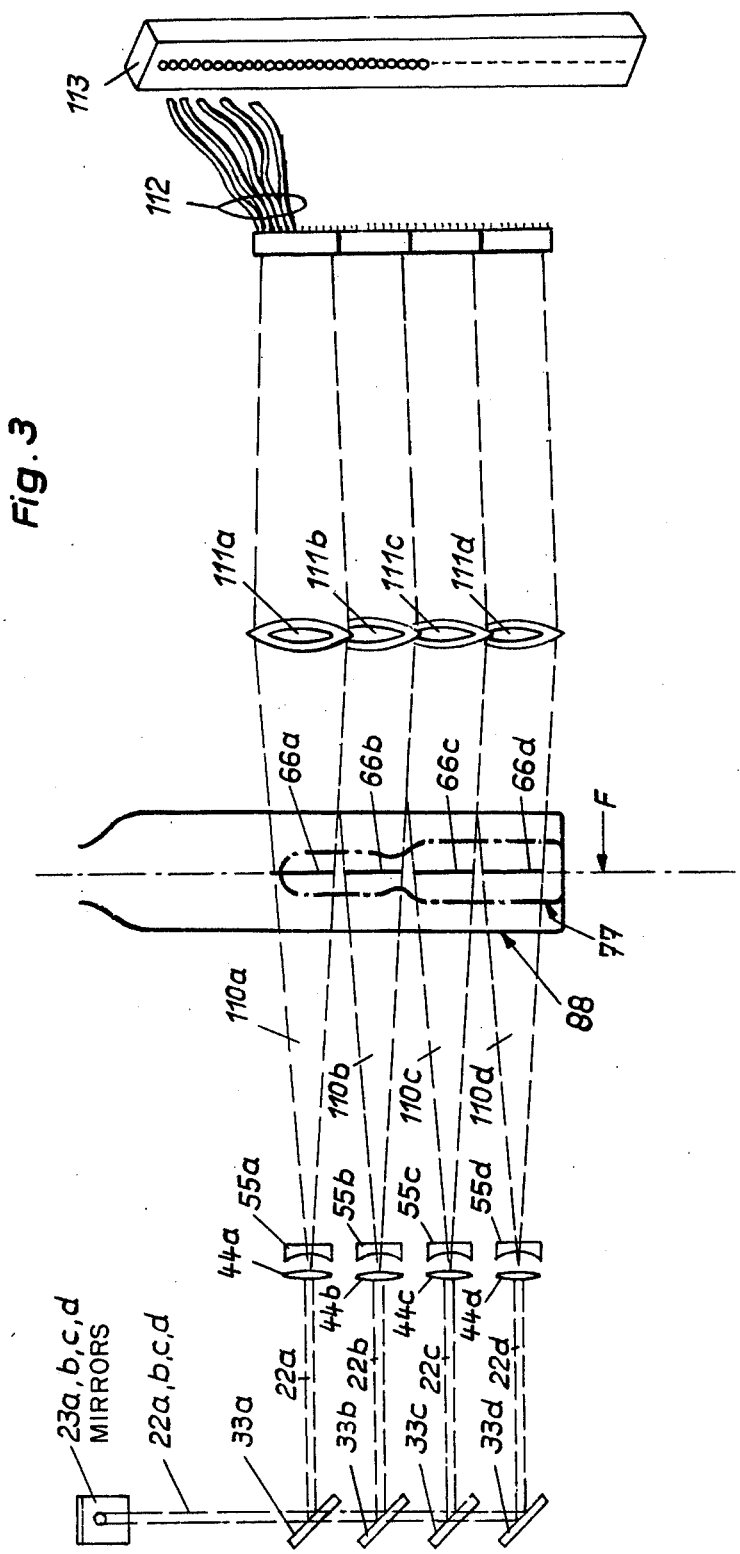

The accompanying drawings show, schematically and by way of example, three embodiments of apparatus according to the invention. In the drawings:

FIG. 1 is a side view of a first embodiment;
FIG. 2 is a plan view of a second embodiment;
FIG. 3 is a side view of the second embodiment;
FIG. 4 is a side view of a third embodiment; and
FIG. 5 is a plan view of the third embodiment.

In the embodiment of FIG. 1, a known source 1 emits a laser beam 2 towards a series of four partially-transparent mirrors 3a, 3b, 3c, 3d which divide beam 2 into four beams 4a, 4b, 4c, 4d which pass through a lens system 5 and converge towards an ampoule 6 to be inspected. This ampoule 6 is mounted vertically in a device 7 which can rotate the ampoule and then stop this rotation for inspection of the ampoule. The beams 4 are disposed in a vertical plane, and each beam has a respective focal point 8a . . . 8d close to the axis 9 of ampoule 6.

After passing through ampoule 6, the beams 4 pass through a lens system 10 and each beam is received by a respective photoelectric cell 11a, 11b, 11c, 11d. Cells 11 influence, in known manner, electrical means 12 which emit a signal 13 as a function of the quality of each beam. In practice, this means that if a beam has met a foreign body in the ampoule 6, the signal 13 actuates a device 14, which may be electro-mechanical, for removing or rejecting an ampoule 6 containing liquid with a foreign particle.

The parts 1, 3, 5, 7, 10, 11, 12 and 14 may be of any known construction.

In the described example, the beams 4 pass through the lens 5 whose focus and numerical aperture are calculated so that the focussing gives an Airy disc or spot for a light cone of maximum length and minimum conicity.

The beams 4 may be angularly regulated, but always in a vertical plane passing through the ampoule 6 to be verified with their focal points 8 situated substantially centrally of the ampoule. Such angular regulation enables the inspected vertical surface to be increased or decreased. Of course, for a given number of beams, the greater the inspected surface, the greater the separation between the beams, and vice versa.

In use, an ampoule 6 to be examined is held vertically, neck up, by a suitable mount of device 7. The device 7 then turns ampoule 6 at high speed to produce centrifuging of the liquid in the ampoule. This centrifuging ensures:

- complete elimination of small air bubbles;
- complete emptying of the possibly-full neck of the ampoule; and
- energetic agitation of the liquid to remove impurities sticking on the wall.

During the rotation of ampoule 6, the photoelectric cells record large modulations due to agitation of the liquid and irregularities in the glass wall of the ampoule. These modulations are not taken into account.

The ampoule 6 is then stopped for inspection. As soon as the ampoule stops, the liquid remaining in the ampoule continues to rotate for a short moment and rotatably drives the impurities to be detected with it. The impurities passing through the laser beams produce modulations of the light on cells 11 which transform the modulations into electric pulses 13. The number and intensity of pulses 13 are recorded and give a standard for rejection or acceptance of the ampoule by device 14.

In the embodiment of FIGS. 2 and 3, a laser source 21 emits a quasi-parallel beam 22 which passes through several partially-transparent mirrors 23a, 23b, 23c, 23d. These mirrors for example have the following degrees of reflection:

23a : 75% transparence and 25% reflection;
23b : 66% transparence and 34% reflection;
23c : 50% transparence and 50% reflection; and
23d : 100% reflection, whereby in this example the light of laser 21 is divided into four beams 22a, 22b, 22c, 22d of substantially the same intensity.

Totally reflecting mirrors 33a, 33b, 33c, 33d (visible on FIG. 3 but not on FIG. 2) disposed at 45°, reflect the partial beams of substantially the same intensity towards astigmatic lens systems each formed by a spherical lens 44a, 44b, 44c and 44d and a cylindrical lens 55a, 55b, 55c and 55d respectively. Each of these lens systems concentrates the light in a horizontal plane at the focus F of the spherical lens but makes it diverge in a plane (vertical in this instance) because of the concave spherical lens (divergent) to give the image of a bar whose length is a function of the divergence of the cylindrical lens and thickness substantially that of the Airy disc or spot at the focus of the spherical lens.

The bars of maximum concentration of the light are at 66a, 66b, 66c, 66d in the axis of the focuses F and arranged coincident with the axis of an ampoule to be examined. Silhouettes of the smallest and largest ampoules to be examined are shown respectively by 77 and 88, axially disposed on F.

As a numerical example, if the primary beam 22 has a diameter of about 1mm and the lens 44(a, b, c, d) a focus of 60mm, the Airy spot will have a diameter of about 0.1mm. If the largest ampoule has a radius of about 10mm, the diameter of the luminous cone (looking in the plane of FIG. 2) on the surface of the ampoule will be about 0.16 to 0.2mm.

Now, this conical section as well as the Airy spot are drawn out heightwise by the cylindrical lens 55 (a, b, c, d). There is thus obtained a narrow, substantially plane and vertical zone which passes completely through the ampoule to be examined, and whose height is arbitrarily chosen.

For constructional reasons, it is more convenient to limit this height to a value suitable for the smallest ampoule, and to superimpose several groups (in this example, four) to examine longer ones.

For constructional reasons, it is also convenient to arrange the four groups of the example in fan configuration centred on axis F, but this arrangement is not a characteristic of the invention.

The beams 110a, 110b, 110c, 110d of the laser, shaped by lenses 44, 55 (a, b, c, d) as described above, are received by converging lenses 111 (a, b, c, d) arranged vertically to reduce the bulk, and whose focuses are such that an enlarged image of the bar 66 (a, b, c, d) is formed on a vertical line at which is placed either a multiple photoelectric cell or, as shown on FIGS. 2 and 3, a series of optical fibre bundles 112, initially adjacent, these bundles individually illuminating a series of photoelectric cells 113.

The device for rotating the ampoules is not shown in FIGS. 2 and 3.

Operation is as follows:

Upon rotation and abrupt stopping of the ampoules, the liquid continues to rotate during a given time together with any impurities which necessarily pass through the narrow luminous vertical zone on axis F. The shadow of these impurities produces a dark spot in the image formed by lenses 111 (a, b, c, d). In this manner, no impurity can pass un-noticed; however a small dark spot on a long luminous "bar" only reduces the overally intensity of the light by a small amount. By fractionning the luminous bar into a series of short zones each examined by an individual photoelectric cell, it is possible to obtain a perceptible variation of light of each impurity, even small ones. It is easy to make the fractionned zones practically adjacent, for example by using optical fibre bundles which initially touch.

It is also possible to connect the photoelectric cells in such a manner as to be only sensitive to brief pulses (passage of an impurity) and to amplify these pulses in the same manner, for whichever cell is de-energized.

The described devices may be entirely automated so as to permit a rapid and reliable selection of the pharmaceutical ampoules for injection.

In the embodiment of FIGS. 4 and 5, the laser beam is not divided.

A laser source (not shown) emits a cylindrical laser beam 51°. A spherical lens 52° concentrate beam 510 at axis X—X and a cylindrical lens 53° vertically spreads the beam 510. The beam is made parallel in a vertical plane by a lens 540.

An ampoule 550 is placed on axis X—X. During examination, the ampoule is rapidly rotated and stopped so that its liquid content remains in rotation.

Beam 510 passes through ampoule 550 and a mirror 560 reflects the beam to a mirror 570 which reflects it to a spherical lens 580. Lens 580 projects onto a photoelectric cell 590 an image of the region of the beam between mirrors 560 and 570, in the form of a blurred vertical bar.

Any dust or particle in the path of the beam, and particularly in ampoule 550 produces a shadow on cell 590. An a.c. amplifier (not shown), to which cell 590 is connected, produces an electric output signal only when such a mobile particle in the liquid of ampoule 550 intercepts the beam. Any stationary spots or stains, such as scratches or streaks on the glass of ampoule 550, do not produce modulations in the light and hence do not produce electric signals.

In the last-described example, the beam passes through the ampoule three times in different locations, by means of the oblique mirrors 560 and 570. Of course, for long ampoules, further mirrors could be used, so that the beam passes through the ampoule 5 times for example.

The mechanical means (not shown) for rotating the ampoules and holding them without rotation along axis X—X are shown. To accelerate the output of the apparatus, it is possible to provide a revolding device for simultaneously rotating several ampoules, and then placing the ampoules one at a time along axis X—X.

The amplifier influenced by cell 590 is of known construction. An automatic system, controlled by this amplifier, can be provided to act on mechanical means for removing or rejecting an ampoule containing a foreign body such as dust.

As an alternative to an electric signal, the electrical means 13 may emit a perceptible optical or acoustic signal for example to permit manual removal of an ampoule containing a foreign particle.

What is claimed is:

1. An apparatus for examining pharmaceutical ampoules containing an injectable liquid, comprising means for holding an ampoule vertically and for rotating the ampoule prior to an examination and holding it without rotation during the examination, a laser source, optical imaging means between said source and the ampoule to produce a laser beam in a vertical plane passing through the whole length of the ampoule, a multiplicity of photoelectric cells disposed to each receive at least a part of the beam having passed through the ampoule, and electrical means influenced by those cells having received light from the laser beam, for emitting a perceptible signal when the beam intercepts a solid particle in the liquid of an ampoule while the ampoule is at rest, said imaging means having a focal point and a numerical aperture enabling a focalization to produce an Airy spot for a conical beam of maximum length and minimum conicity, and said imaging means comprising a spherical beam-inlet lens and a cylindrical beam-outlet lens arranged to project a luminous bar in a focal axis at the center of an ampoule to be examined, the bar thickness being substantially that of the Airy spot at the focus of each spherical lens and at least one oblique mirror arranged in the path of the beam so that the beam passes through the ampoule at least two times each time at a different location.

* * * * *